United States Patent [19]
Ganguly et al.

[11] 4,279,896
[45] Jul. 21, 1981

[54] NOVEL 20-IMINO MACROLIDE ANTIBACTERIAL AGENTS

[75] Inventors: Ashit K. Ganguly, Upper Montclair; Yi-Tsung Liu, Morris County, both of N.J.

[73] Assignee: Schering Corporation, Kenilworth, N.J.

[21] Appl. No.: 161,947

[22] Filed: Jun. 23, 1980

[51] Int. Cl.³ .................... A61K 31/71; C07H 17/08
[52] U.S. Cl. .................... 424/180; 536/17 R; 424/181
[58] Field of Search ............. 536/17 R; 424/180, 181

[56] References Cited

U.S. PATENT DOCUMENTS 3,975,372  8/1976  Ganguly et al. .................. 536/17 R
4,056,616  11/1977  Reimon et al. .................. 536/17 R
4,161,523  7/1979  Weinstem et al. ................ 536/17 R

OTHER PUBLICATIONS

Derwent Abstract 71395Y, Japanese Pat. No. 2100483, 1977.
Derwent Abstract 71396Y, Japanese Pat. No. 2100485, 1977.

Primary Examiner—Johnnie R. Brown
Assistant Examiner—Blondel Hazel
Attorney, Agent, or Firm—Carver C. Joyner

[57] ABSTRACT

Rosaramicin and 12,13-desepoxy-12,13-dehydrorosaramicin form novel 20-imino-20-deoxy derivatives having substantial antibacterial activity. Methods for preparing such compounds are also disclosed.

57 Claims, No Drawings

NOVEL 20-IMINO MACROLIDE ANTIBACTERIAL AGENTS

This invention relates to a novel class of macrolide antibacterial agents. More particularly, this invention relates to heterocyclic 20-imino-20-deoxyrosaramicin and to 20-imino-20-deoxy-12,13-desepoxy-12,13 dehydrorosaramicin.

U.S. Pat. Nos. 4,056,616 and 4,161,523 disclose rosamicin and 12,13-desepoxy 12,13-dehydro rosamicin and certain derivatives thereof. Rosamicin is now known as rosaramicin.

We have now discovered that certain heterocyclic imino derivatives of these compounds possess potent and broad spectrum antibacterial activity.

DESCRIPTION OF THE INVENTION

In its composition of matter aspect, this invention embraces compounds of the following formula:

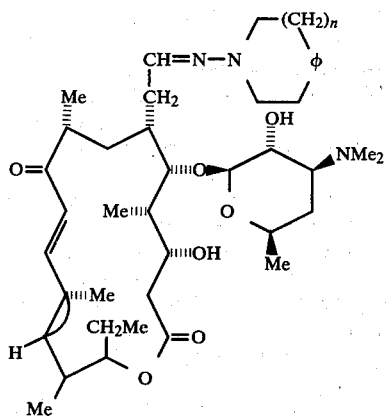

Wherein D, bridging positions 12 and 13 represents a double bond or an oxirane ring; Q is a member of the group consisting of $CH_2, CRR_1$, NH, NR, O, S, $SO_2$,

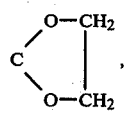

CHOH, CHOR, $CROR_1$, $$CROC\!\!-\!\!R_1,$$
$$\|$$
$$O$$

CHCOOH, CHCOOR, $CHCONH_2$, and $CHCONRR_1$; R and $R_1$ may be the same or different, each being a member of the group consisting of ($C_1$-$C_8$) alkyl, ($C_7$-$C_{10}$) aralkyl and ($C_6$-$C_{10}$) aryl including X-substituted aryl and aralkyl, wherein X is a member of the group consisting of halogen, trifluoromethyl, ($C_1$-$C_5$) alkoxy, and ($C_1$-$C_5$) alkycarbonyl; and n is an integer of the group consisting of 0, 1 and 2.

In its process aspect, this invention embraces administering to a mammal having a bacterial infection, a therapeutically effective dose of a compound as defined for formula 1.

In order to elicit an antibacterial effect, the compounds of this invention may be administered orally, topically, intramuscularly or intravenously. Administration may be effected by the use of tablets, capsules, elixirs and injectable suspensions and solutions. Each of these dosage forms may be admixed with non-toxic pharmaceutically acceptable excipients generally used in the art. The compounds of this invention may advantageously be administered at from about 5 mg to about 50 mg per kg. per day in divided doses.

The compounds of this invention are broad spectrum antibacterial agents exhibiting significant activity against numerous strains of Staphylococcus, Streptococcus, Enterobacter, *Eschericia Coli*, Bacillus, Pseudomonas, Clostridium and Corynebacterium. Included among these bacteria are *Strep. pyogenes C*, Staph 209P, *Staph. Wood, Strept Karipedes,* Enterobacter 1022, *E. Coli* 10536, and *Klebsiella Rahal* 3. Some of the foregoing bacteria are clinical isolates obtained from patients having active infections.

PREPARATION OF THE 1-AMINO REACTANTS

Many of the 1-amino reactants herein utilized for condensation with the 20-aldehyde function of rosaramicin or 12,13-desepoxy-12,13-dehydrorosaramicin are commercially available. Those that must be synthesized may be prepared by one of the following general procedures.

(A) J.H. Biel, et. al., J. Org. Chem., 26 4096 (1961)

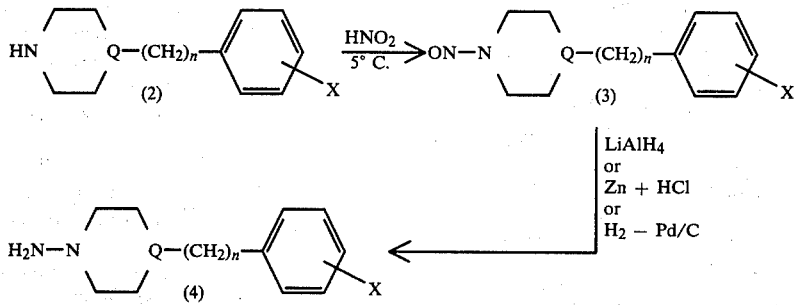

(B) R. Gosl et. al., Org. Syn., Collec. Vol. V. 43, (1963).

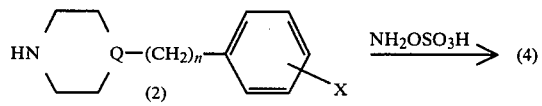

Wherein Q, X and n are as previously defined. The reactants wherein the cyclic amino group is a 5 membered (n=0), or a seven membered (n=2) ring may be prepared analogously.

EXAMPLE I

20-[(4,4-Dioxo-4-thiomorpholino)imino]-20-deoxyrosaramicin

Dissolve 1.09 g. of rosaramicin and 275 mg. of N-amino-4, 4-dioxo-4 thiomorpholine in 50 ml of absolute ethanol. Stir the reaction mixture at room temperature for two days. Collect the white precipitate by filtration and crystallize from methanol.

Yield 885 mg. m.p. 180° C. $[\alpha]D^{36°} = -29.1$ M=713

EXAMPLE II

20-[(4-Hydroxypiperidyl)imino]-20-deoxy rosaramicin

Dissolve 581 mg. of rosaramicin in 15 ml. of ethanol with stirring and add 120 mg. of 1-amino-4-hydroxypiperidine. Stir the reaction mixture at room temperature (20° C.) for 20 hours and evaporate. Dissolve the resulting yellow syrup in chloroform and chromatograph on a column containing 100 g. of silica gel. Develop the column using a solvent system consisting of 10% methanol in chloroform followed by 15% methanol in chloroform. Combine the fractions in accordance with the $R_f$'s on silica gel plates using 5% methanol in chloroform to obtain thereby the product of this example, plus some unreacted rosaramicin.

In a similar manner, subject an equivalent quantity of the following 1-amino reactants to the process of the foregoing examples to obtain thereby the corresponding substituted 20-imino-20-deoxy derivatives:
N-amino-piperidine,
1-amino-4-methylpiperidine,
1-amino-4,4-ethylenedioxypiperidine,
1-amino-4-benzyloxypiperidine,
1-amino-4-methoxypiperidine,
1-amino-4-acetyloxypiperidine,
1-amino-4-methyl-4-hydroxypiperidine,
1-amino-4-ethyl-4-propionyloxypiperidine,
1-amino-4-propyl-4-ethoxypiperidine,
1-amino-4-phenethylpiperidine,
1-amino-4-benzoyloxypiperidine,
1-amino-4-butoxycarbonylpiperidine,
1-amino-4-carboxypiperidine,
1-amino-4-dimethylaminocarbonylpiperidine,
1-amino-4-methylpiperazine,
1-amino-4-benzylpiperazine,
1-amino-4-phenethylpiperazine,
N-aminomorpholine
N-amino-4-thiomorpholine
1-amino-4-(β-hydroxyethyl) piperazine
1-amino-4-carbamoylpiperidine
N-aminopyrrolidine
N-aminohomopiperidine
1-amino-2,6-dimethylpiperidine,
N-aminorhodanine
1-aminohydantoin
1-amino-4-phenylpiperidine,
1-amino-4-hydroxy-4-phenylpiperidine,
1-amino-4-cyano-4-phenylpiperidine,
1-amino-4-(P-chlorophenyl)-4-hydroxypiperidine,
1-amino-4-(P-chlorophenyl)-3,4-dehydropiperidine,
1-amino-4-(o-tolyl)piperazine,
1-amino-4-(m-tolyl)piperazine,
1-amino-4-(ααα-trifluoro-m-tolyl)piperazine,
1-amino-4-(benzyl)piperazine,
1-amino-4-(P-chlorobenzhydryl)piperazine,
1-amino-4-(phenyl)-3,4-dehydropiperidine,
1-amino-4-benzylpiperidine,
1-amino-4-phenylpiperazine,
1-amino-4-(p-fluorophenyl)piperazine,
1-amino-4-(O-chlorophenyl)piperazine,
1-amino-4-(m-chlorophenyl)piperazine,
1-amino-4-(p-chlorophenyl)piperazine,
1-amino-4-(O-methoxyphenyl)piperazine,
1-amino-4-(p-methoxyphenyl)piperazine, and
1-amino-4-(p-acetylphenyl)piperazine.

Isolate the products in the manner described in the foregoing examples to obtain thereby the following:
20-[(piperidyl)imino]-20-deoxy rosaramicin,
20-[(4-methylpiperidyl)imino]-20-deoxy rosaramicin,
20-[(4,4-ethylenedioxypiperidyl)imino]-20-deoxy rosaramicin,
20-[(4-benzyloxypiperidyl)imino]-20-deoxy rosaramicin,
20-[(4-methoxypiperidyl)imino]-20-deoxy rosaramicin,
20-[(4-acetyloxypiperidyl)imino]-20-deoxy rosaramicin,
20-[(4-methyl-4-hydroxypiperidyl)imino]-20-deoxy rosaramicin,
20-[(4-ethyl-4-propionyloxypiperidyl)imino]-20-deoxy rosaramicin,
20-[(4-propyl-4-ethoxypiperidyl)imino]-20-deoxy rosaramicin,
20-[(4-phenethylpiperidyl)imino]-20-deoxy rosaramicin,
20-[(4-benzoyloxypiperidyl)imino]-20-deoxy rosaramicin,
20-[(4-butoxycarbonylpiperidyl)imino]-20-deoxy rosaramicin,
20-[(4-carboxypiperidyl)imino]-20-deoxy rosaramicin,
20-[(4-dimethylaminocarbonylpiperidyl)imino]-20-deoxy rosaramicin,
20-[(4-methylpiperazinyl)imino]-20-deoxy rosaramicin,
20-[(4-benzylpiperazinyl)imino]-20-deoxy rosaramicin,
20-[(4-phenethylpiperazinyl)imino]-20-deoxy rosaramicin,
20-[(morpholino)imino]-20-deoxy rosaramicin,
20-[(thiomorpholino)imino]-20-deoxy rosaramicin,
20-[(4-β-hydroxyethylpiperazinyl)imino]-20-deoxy rosaramicin,
20-[(4-carbamoylpiperidyl)imino]-20-deoxy rosaramicin,
20-[(pyrrolidyl)imino]-20-deoxy rosaramicin,
20-[(homopiperidyl)imino]-20-deoxy rosaramicin,
20-[(2,6-dimethylpiperidyl)imino]-20-deoxy rosaramicin,
20-[(4-oxo-2-thioxo-3-thiazolidinyl)imino]-20-deoxy rosaramicin, 20-[(2,4-dioxoimidazolidinyl)imino]-20-deoxy rosaramicin,
20-[(4-phenylpiperidyl)imino]-20-deoxy rosaramicin,
20-[(4-hydroxy-4-phenylpiperidyl)imino]-20-deoxy rosaramicin,
20-[(4-cyano-4-phenylpiperidinyl)imino]-20-deoxy rosaramicin,
20-{[4-(P-chlorophenyl)-4-hydroxypiperidyl]imino}-20-deoxyrosaramicin,
20-{[4-(P-chlorophenyl)-3,4-dehydropiperidyl]imino}-20-deoxyrosaramicin,
20-{[4-(o-tolyl)piperazinyl]imino}-20-deoxy rosaramicin,
20-{[4-(m-tolyl)piperazinyl]imino}-20-deoxy rosaramicin,
20-{[4-α,α,α trifluoro-m-tolyl)piperazinyl]imino}-20-deoxyrosaramicin,
20-{[4-(benzyl)piperazinyl]imino}-20-deoxy rosaramicin,
20-{[4-(p-chlorobenzhydryl)piperazinyl]imino}-20-deoxy rosaramicin,
20-{[4-(phenyl)-3,4-dehydropiperidyl]imino}-20-deoxy rosaramicin,
20-[(4-benzylpiperidyl)imino]-20-deoxy rosaramicin,
20-[(4-phenylpiperazinyl)imino]-20-deoxy rosaramicin,
20-{[4-(P-fluorophenyl)piperazinyl]imino}-20-deoxy rosaramicin,
20-{[4-(O-chlorophenyl)piperazinyl]imino}-20-deoxy rosaramicin,
20-{[4-(m-chlorophenyl)piperazinyl]imino}-20-deoxy rosaramicin,
20-{[4-(P-chlorophenyl)piperazinyl]imino}-20-deoxy-rosaramicin,
20-{[4-(O-methoxyphenyl)piperazinyl]imino}-20-deoxy rosaramicin,
20-{[4-(P-methoxyphenyl)piperazinyl]imino}-20-deoxy rosaramicin and
20-{[4-(P-acetylphenyl)piperazinyl]imino}-20-deoxy rosaramicin.

In a similar manner, by reacting 12,13-desepoxy-12,13-dehydrorosaramicin with the 1-amino reactants set forth above under the conditions described in the examples, the corresponding 12,13-desepoxy-12,13-dehydro-20-imino-20-deoxy rosaramicin derivatives may be prepared.

We claim:
1. A compound of the formula:

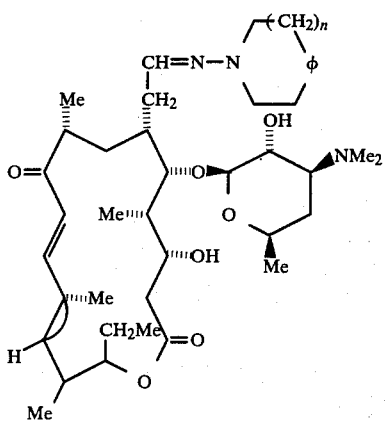

Wherein D, bridging positions 12 and 13 represents a double bond or an oxirane ring; Q is a member of the group consisting of $CH_2$, $CRR_1$, NH, NR, O, S, $SO_2$,

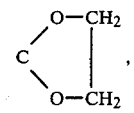

CHOH, CHOR, $CROR_1$,

CHCOOH, CHCOOR, $CHCONH_2$, and $CHCONRR_1$; R and $R_1$ may be the same or different, each being a member of the group consisting of ($C_1$–$C_8$) alkyl, ($C_7$–$C_{10}$) aralkyl and ($C_6$–$C_{10}$) aryl including X-substituted aryl and aralkyl, wherein X is a member of the group consisting of halogen, trifluoromethyl, ($C_1$–$C_5$) alkoxy, and ($C_1$–$C_5$) alkylcarbonyl; and n is an integer of the group consisting of 0, 1 and 2.

2. A compound of claim 1 wherein D bridging positions 12 and 13 represents an oxirane ring and Q, R, $R_1$ and n are as defined in said claim 1.

3. A compound of claim 1 wherein D bridging positions 12 and 13 represents a double bond and Q, R, $R_1$ and n are as defined in said claim 1.

4. A compound of claim 2 wherein n is 0 and Q, R and $R_1$ are as defined in said claim 2.

5. A compound of claim 2 wherein n is 1 and Q, R and $R_1$ are as defined in said claim 2.

6. A compound of claim 2 wherein n is 2 and Q, R and $R_1$ are as defined in claim 2.

7. A compound of claim 3 wherein n is 1 and Q, R and $R_1$ are as defined in said claim 3.

8. A compound of claim 3 wherein n is 0 and Q, R and $R_1$ are as defined in said claim 3.

9. A compound of claim 3 wherein n is 2 and Q, R and $R_1$ are as defined in said claim 3.

10. The compound of claim 4 wherein the heterocycle is 2,4-dioxoimidazolidine, said compound being 20-[2,4-dioxoimidazolidinyl)imino]-20-deoxy rosaramicin.

11. The compound of claim 4 wherein the heterocycle is 4-oxo-2-thioxo-3-thiazolidine, said compound being 20-[(4-oxo-2-thioxo-3-thiazolinyl)imino]-20-deoxy rosaramicin.

12. A compound of claim 4 wherein Q is $CH_2$, said compound being 20-[(pyrrolidyl)imino]-20-deoxy rosaramicin.

13. The compound of claim 5 wherein Q is $CH_2$, said compound being 20-[(piperidyl)imino]-20-deoxyrosaramicin.

14. The compound of claim 5 wherein Q is NH, said compound being 20-[(piperazinyl)imino]-20-deoxyrosaramicin, 15. The compound of claim 5 wherein Q is O, said compound being 20-[(morpholino)imino]-20-deoxyrosaramicin.

16. The compound of claim 5 wherein Q is S, said compound being 20-[(thiomorpholino)imino]-20-deoxyrosaramicin.

17. The compound of claim 5 wherein Q is $SO_2$, said compound being 20-[(4,4-dioxo-4-thiomorpholino)imino]-20-deoxyrosaramicin.

18. The compound of claim 5 wherein Q is

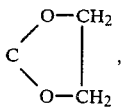

said compound being 20-[(4,4-ethylenedioxypiperidyl)imino]-20-deoxyrosaramicin.

19. The compound of claim 5 wherein Q is CHOH, said compound being 20-[(4-hydroxypiperidyl)imino]-20-deoxyrosaramicin.

20. The compound of claim 5 wherein Q is CHOCH$_3$, said compound being 20-[(4-methoxypiperidyl)imino]-20-deoxyrosaramicin.

21. The compound of claim 5 wherein Q is CH—O—COCH$_3$, said compound being 20-[(4-acetoxypiperidyl)imino]-20-deoxyrosaramicin.

22. The compound of claim 5 wherein Q is

said compound being 20-[(4-ethyl-4-hydroxypiperidyl)imino]-20-deoxyrosaramicin.

23. The compound of claim 5 wherein Q is

said compound being 20-[(4-ethyl-4-methoxypiperidyl)imino]-20-deoxyrosaramicin.

24. The compound of claim 5 wherein Q is

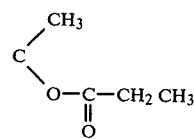

said compound being 20-[(4-methyl-4-propionyloxypiperidyl)imino]-20-deoxyrosaramicin.

25. The compound of claim 5 wherein Q is CHCO$_2$H, said compound being 20-[(4-carboxypiperidyl)imino]-20-deoxyrosaramicin.

26. The compound of claim 5 wherein Q is CHCO$_2$CH$_3$, said compound being 20-[(4-methoxycarbonylpiperidyl)imino]-20-deoxyrosaramicin.

27. The compound of claim 5 wherein Q is CHCONH$_2$, said compound being 20-[(4-carbamoylpiperidyl)imino]-20-deoxyrosaramicin.

28. The compound of claim 5 wherein Q is CHCON(CH$_3$)$_2$, said compound being 20-[(4-dimethylaminocarbonylpiperidyl)imino]-20-deoxyrosaramicin.

29. The compound of claim 5 wherein Q is N—CH$_3$, said compound being 20-[(4-methylpiperazinyl)imino]-20-deoxyrosaramicin.

30. The compound of claim 7 wherein Q is CH$_2$, said compound being 12,13-desepoxy-12,13-dehydro-20-[(piperidyl)imino]-20-deoxyrosaramicin.

31. The compound of claim 7 wherein Q is NH, said compound being 12,13-desepoxy-12,13-dehydro-20-[(piperazinyl)imino]-20-deoxyrosaramicin.

32. The compound of claim 7 wherein Q is N—CH$_3$, said compound being 12,13-desepoxy-12,13-dehydro-20-[(4-methylpiperazinyl) imino]-20-deoxyrosaramicin.

33. The compound of claim 7 wherein Q is O, said compound being 12,13-desepoxy-12,13-dehydro-20-[(morpholino)imino]-20-deoxyrosaramicin.

34. The compound of claim 7 wherein Q is S, said compound being 12,13-desepoxy-12,13-dehydro-20-[(thiomorpholino)imino]-20-deoxyrosaramicin.

35. The compound of claim 7 wherein Q is SO$_2$, said compound being 12,13-desepoxy-12,13-dehydro-20-[(4,4-dioxo-4-thiomorpholino)imino]-20-deoxyrosaramicin.

36. The compound of claim 7 wherein Q is

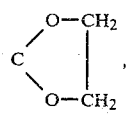

said compound being 12,13-desepoxy-12,13-dehydro-20-[(4-ethylenedioxypiperidyl)imino]-20-deoxyrosaramicin.

37. The compound of claim 7 wherein Q is CHOH, said compound being 12,13-desepoxy-12,13-dehydro-20-[(4-hydroxypiperidyl)imino]-20-deoxyrosaramicin.

38. The compound of claim 7 wherein Q is CH—OC$_2$H$_5$, said compound being 12,13-desepoxy-12,13-dehydro-20-[(4-ethoxypiperidyl)imino]-20-deoxyrosaramicin.

39. The compound of claim 7 wherein Q is CHO—COC$_6$H$_5$, said compound being 12,13-desepoxy-12,13-dehydro-20-[(4-benzoyloxypiperidyl)imino]-20-deoxyrosaramicin.

40. The compound of claim 7 wherein Q is

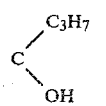

said compound being 12,13-desepoxy-12,13-dehydro-20-[(4-propyl-4-hydroxypiperidyl)imino]-20-deoxyrosaramicin.

41. The compound of claim 7 wherein Q is

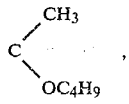

said compound being 12,13-desepoxy-12,13-dehydro-20-[(4-methyl-4-butoxypiperidyl)imino]-20-deoxyrosaramicin.

42. The compound of claim 7 wherein Q is

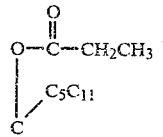

said compound being 12,13-desepoxy-12,13-dehydro-20-[(4-pentyl-4-propionyloxypiperidyl)imino]-20-deoxyrosaramicin.

43. The compound of claim 7 wherein Q is $CHCO_2H$, said compound being 12,13-desepoxy-12,13-dehydro-20-[(4-carboxypiperidyl)imino]-20-deoxyrosaramicin.

44. The compound of claim 7 wherein Q is $CHCO_2CH_3$, said compound being 12,13-desepoxy-12,13-dehydro-20-[(4-methoxycarbonylpiperidyl)imino]-20-deoxyrosaramicin.

45. The compound of claim 7 wherein Q is $CHCONH_2$, said compound being 12,13-desepoxy-12,13-dehydro-20-[(4-carbamoylpiperidyl)imino]-20-deoxyrosaramicin.

46. The compound of claim 7 wherein Q is $CHCON(CH_3)_2$, said compound being 12,13-desepoxy-12,13-dehydro-20-[(4-dimethylaminocarbonylpiperidyl)imino]-20-deoxyrosaramicin.

47. The compound of claim 6 wherein Q is $CH_2$, said compound being 20-[(homopiperidyl)imino]-20-deoxyrosaramicin.

48. A method of eliciting an antibacterial response in a mammal having a bacterial infection which comprises administering to the mammal a therapeutically effective quantity of a compound of the formula:

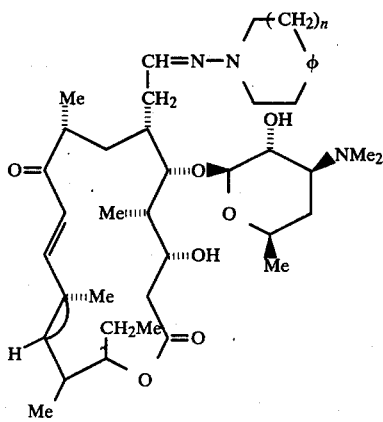

Wherein D bridging positions 12 and 13 represents a double bond or an oxirane ring; Q is a member of the group consisting of $CH_2$, $CRR_1$, $NH$, $NR$, $O$, $S$, $SO_2$,

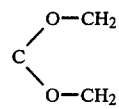

CHOH, CHOR,

CROR,

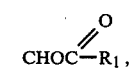

CHCOOH, CHCOOR, $CHCONH_2$, and $CHCONRR_1$; Wherein R and $R_1$ may be the same or different, each being a member of the group consisting of ($C_1$–$C_8$) alkyl, ($C_7$–$C_{10}$) aralkyl and ($C_6$–$C_{10}$) aryl including X-substituted aryl and aralkyl wherein X is a member of the group consisting of halogeno, trifluoromethyl, ($C_1$–$C_5$) alkoxy and ($C_1$–$C_5$) alkylcarbonyl, and N is an integer of the group consisting of 0, 1 and 2.

49. A method according to claim 48 wherein D bridging positions 12 and 13 represents an oxirane ring and Q, R, R, and n are as defined in said claim 48.

50. A method according to claim 48 wherein D bridging positions 12 and 13 represents a double bond and Q, R, $R_1$ and n are as defined in said claim 48.

51. A method according to claim 48 wherein 20-[(4-methylpiperazinyl)imino]-20-deoxyrosaramicin is administered.

52. A method according to claim 48 wherein 20-[(4,4-dioxo-4-thiomorpholino)imino]-20-deoxyrosaramicin is administered.

53. A method according to claim 48 wherein 20-[(4,4-ethylenedioxypiperidinyl)imino]-20-deoxyrosaramicin is administered.

54. A method according to claim 48 wherein 20-[(4-hydroxypyperidyl)imino]-20-deoxyrosaramicin is administered.

55. A method according to claim 48 wherein 20-[(thiomorphilino)imino]-20-deoxyrosaramicin is administered.

56. A method according to claim 48 wherein 12,13-desepoxy-12,13-dehydro-20-[(4-thiomorpholino)imino]-20-deoxyrosaramicin is administered.

57. A method according to claim 48 wherein 12,13-desepoxy-12, 13-dehydro-20-[(4,4-dioxo-4-thiomorpholino)imino]-20-deoxyrosaramicin is administered.

* * * * *